(12) United States Patent
Brajnovic

(10) Patent No.: US 7,845,946 B2
(45) Date of Patent: Dec. 7, 2010

(54) METHOD AND ARRANGEMENT FOR ORIENTING A BRIDGE IN POSITION RELATIVE TO A DENTAL IMPLANT

(75) Inventor: Izidor Brajnovic, Gothenburg (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 0 days.

(21) Appl. No.: 10/584,426

(22) PCT Filed: Nov. 22, 2004

(86) PCT No.: PCT/SE2004/001553

§ 371 (c)(1),
(2), (4) Date: May 23, 2007

(87) PCT Pub. No.: WO2005/060862

PCT Pub. Date: Jul. 7, 2005

(65) Prior Publication Data

US 2007/0281277 A1 Dec. 6, 2007

(30) Foreign Application Priority Data

Dec. 22, 2003 (SE) .................................... 0303461

(51) Int. Cl.
*A61C 8/00* (2006.01)

(52) U.S. Cl. ..................................................... 433/174

(58) Field of Classification Search ......... 433/172–176, 433/215, 219
See application file for complete search history.

(56) References Cited

U.S. PATENT DOCUMENTS

| 5,022,860 | A | * | 6/1991 | Lazzara et al. | 433/174 |
| 5,145,371 | A | * | 9/1992 | Jorneus | 433/173 |
| 5,302,125 | A | * | 4/1994 | Kownacki et al. | 433/172 |
| 5,458,488 | A | * | 10/1995 | Chalifoux | 433/173 |
| 5,549,475 | A | * | 8/1996 | Duerr et al. | 433/173 |
| 5,733,124 | A | | 3/1998 | Kwan | |
| 5,888,218 | A | * | 3/1999 | Folsom | 623/16.11 |
| 5,947,733 | A | * | 9/1999 | Sutter et al. | 433/173 |
| 6,068,479 | A | * | 5/2000 | Kwan | 433/173 |
| 6,142,782 | A | * | 11/2000 | Lazarof | 433/174 |

FOREIGN PATENT DOCUMENTS

| WO | WO 97/34543 | 9/1997 |
| WO | WO 98/32393 | 7/1998 |

* cited by examiner

*Primary Examiner*—Cris L Rodriguez
*Assistant Examiner*—Yogesh Patel
(74) *Attorney, Agent, or Firm*—Knobbe Martens Olson & Bear, LLP

(57) ABSTRACT

A method is provided for orienting a bridge in position relative to a dental implant with the aid of spacer members. The spacer members are brought into cooperation with, on the one hand, the respective implant and, on the other hand, with fastening members arranged in the bridge. A first sleeve-shaped part included in the spacer member is bought into cooperation with the implant. A second sleeve-shaped part included in the spacer member is brought into cooperation with, on the one hand, the first sleeve-shaped part and, on the other hand, with a fastening member in the bridge. The sleeve-shaped parts are made to assume assembled positions when the bridge is anchored to the implants.

24 Claims, 2 Drawing Sheets

US 7,845,946 B2

METHOD AND ARRANGEMENT FOR ORIENTING A BRIDGE IN POSITION RELATIVE TO A DENTAL IMPLANT

PRIORITY INFORMATION

This application is a U.S. National Phase of International Application No. PCT/SE2004/001553, filed Nov. 22, 2004, which claims the benefit of Swedish Application No. SE 0303461-8, filed Dec. 22, 2003.

FIELD OF THE INVENTION

The present invention relates, inter alia, to a method for orienting a bridge in position relative to a dental implant with the aid of a spacer member which is brought into cooperation with, on the one hand, the respective implant and, on the other hand, with fastening members arranged in the bridge. The invention also relates to an arrangement for orienting a bridge in position relative to a dental implant and comprising a spacer member which on the one hand cooperates with the respective implant and on the other hand permits position orientation through cooperation with fastening members arranged in the bridge.

DESCRIPTION OF THE RELATED ART AND SUMMARY OF THE INVENTION

The present invention is a further development of patent application WO 03/061512 filed by the same Applicant and with the same inventor as the present patent application. Concerning the structure of the bridge and the problems of connecting such a bridge, reference is made inter alia to said patent application.

In accordance with the content of the proposed patent application, it may be necessary to use different lengths of spacer sleeves in different installation situations. Quite generally, there is a requirement to be able to reduce the number of components in dental work. With different numbers of components for different installation situations, there are also risks of the components being mixed up, which entails a risk of a substandard installation result and means that certain operations on the bridge or tooth have to be repeated. There is also a requirement for greater variations as regards the configurations of the dental bridge. In some cases, there is a need for all or part of the bridge to be made relatively narrow. There is also a requirement for the mutual parallelism between the implants to be present also in the actual bridge construction. There is also a requirement for the installation work to be able to be continued without the biological incorporation between jaw bone/soft tissue (gum) and the actual parts of the implant and the spacer sleeve having to be interrupted when this has progressed some way. Such interruptions of the incorporation can cause damage which leads to bone absorption, which in turn leads to poorer esthetic results.

The object of the present invention is to solve the above-mentioned problems, inter alia.

That which can principally be regarded as characterizing a method according to the invention is, inter alia, that a first sleeve-shaped part included in the spacer member for the respective implant is brought into cooperation with the implant, and a second sleeve-shaped part included in the spacer member for the respective implant is brought into cooperation with, on the one hand, the first sleeve-shaped part and, on the other hand, with a fastening member in the bridge. Further characteristics are that the first and second sleeve-shaped parts are made to assume assembled positions when the bridge is anchored to the implants, and, upon detachment of the bridge from the implant, the first and second sleeve-shaped parts are separated so that the first sleeve-shaped part maintains its position on the respective implant, and the second sleeve-shaped part follows along with the bridge or constitutes a free part.

That which can principally be regarded as characterizing an arrangement according to the invention is that the spacer member for the respective implant comprises first and second sleeve-shaped parts, where the first sleeve-shaped part cooperates with the implant and the second sleeve-shaped part can be joined to and separated from the first sleeve-shaped part and has a portion which can cooperate with the fastening member in the bridge. Further characteristics are that the first sleeve-shaped part can have a longitudinal extent which is related to the installation situation and is preferably shortened in relation to the second sleeve-shaped part.

In further developments of the inventive concept, the first sleeve-shaped part can have a length (or height) which substantially corresponds to a thickness of the soft tissue or gum on the jaw, in which the respective implant is to be applied. In a preferred embodiment, the first sleeve-shaped part can be arranged in relation to and can cooperate with fibers of the gingiva and, if appropriate, the periosteum. The first sleeve-shaped part can cooperate with the implant via an upper flange surface on the latter. The second sleeve-shaped part can be engaged on the first sleeve-shaped part. The second sleeve-shaped part preferably has a narrowed part extending toward or into the bridge for the purpose of cooperating with the fastening member thereof.

Further embodiments of the invention are set out inter alia in the attached dependent claims concerning the novel arrangement.

By means of what has been proposed above, advantages are obtained which permit great freedom in the procurement and use of the components in connection with thee installation of carbon fiber bridges. Accurate components can be obtained and used. The conditions for a good installation result with very good esthetics can be achieved at the same time as possibilities for a greater number of variations of bridges, for example also narrow ones.

A presently proposed embodiment of a method and an arrangement according to the invention will be described below with reference to the attached drawings, in which

DETAILED DESCRIPTION OF THE PREFERRED EMBODIMENTS

Figure 1:
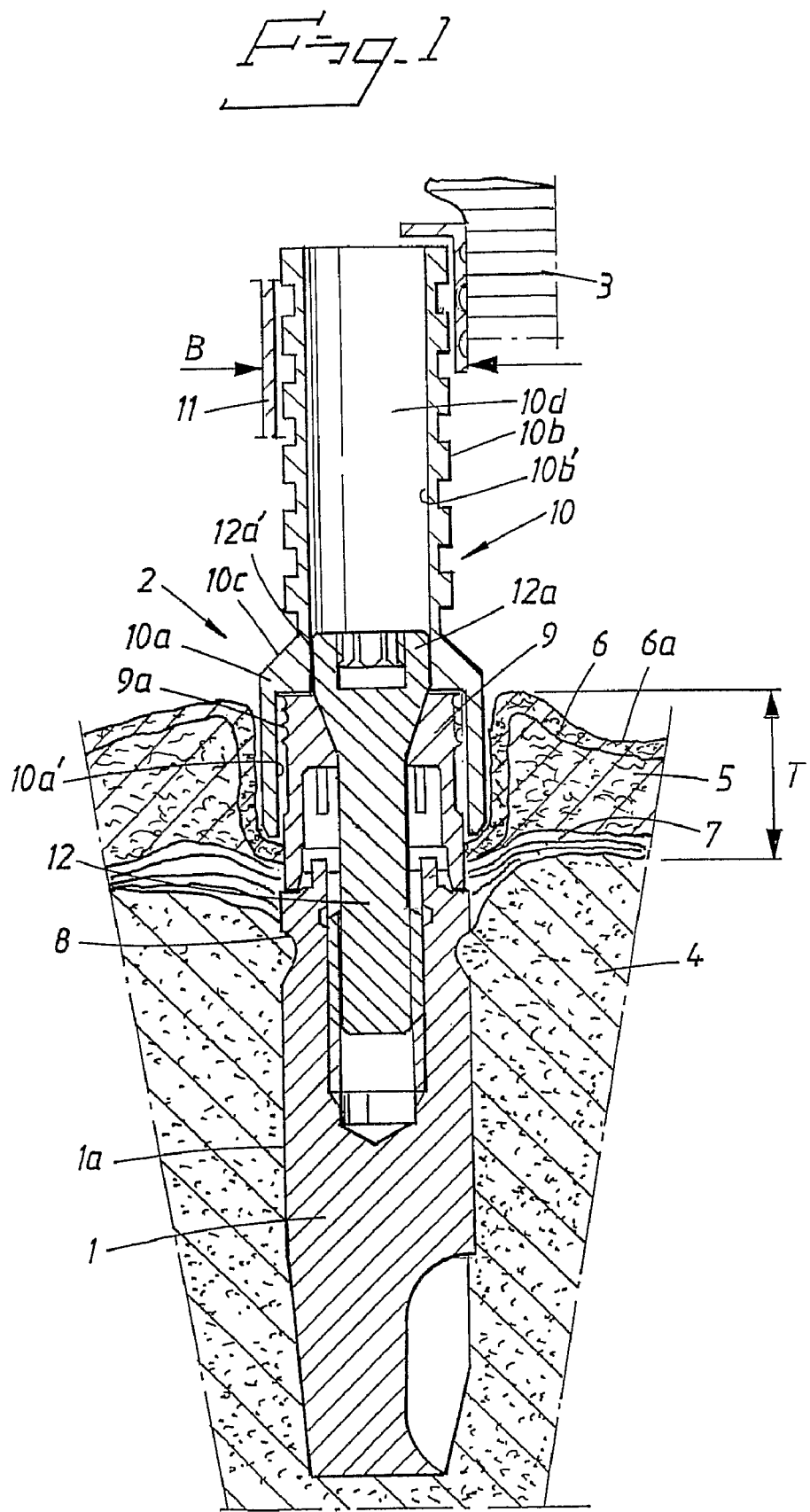
FIG. 1 shows a vertical section through an implant in a bridge, with a spacer member comprising first and second sleeve-shaped parts.

In FIG. 1, an implant is indicated by 1. Spacer members connected to the implant are indicated by 2. Parts of a carbon fiber bridge are shown by 3. The bridge or equivalent is anchored to two or more implants according to FIG. 1. Only one implant with associated spacer member is shown in FIG. 1, since the different implants and spacer members can have the same or essentially the same structures. Reference is made here to the aforementioned WO document. The implant is anchored in a jaw bone which is indicated symbolically by 4 and which is provided at the top with a gum 5 or soft tissue. The oral epithelium of the gum is indicated by 6, and the fibers in the gingiva of the gum are indicated by 7. In addition, periosteum around the outer surface 1a of the implant has been indicated by 8. The implant can be anchored in the jaw bone 4 in a manner known per se, for example by means of outer threads (not shown) on the implant. The implant can be screwed into the jaw bone via a preliminary threading in the latter. Alternatively, the implant can be of the self-tapping kind. The spacer member of the respective implant can comprise a first sleeve-shaped part 9 and a second sleeve-shaped part 10. The first sleeve-shaped part can have grooves 9a. The second sleeve-shaped part has a first part 10a and a second part 10b. The first part 10a has the form of a sleeve which can be engaged over the first sleeve-shaped part 9. The sleeve-shaped part 10a thus encloses the grooves 9a. On its outside, the second sleeve-shaped part has an inclined outer surface 10c. The first sleeve-shaped part 9 has a low height and, in the state shown in FIG. 1, is substantially level with the top surface 6a of the epithelium 6 at the spacer member. The first part 10a of the second sleeve-shaped part has an extent in length or height which only slightly exceeds the length or height of the first sleeve-shaped part. The inclination 10c can be considered to essentially adjoin the top surface 6a of the epithelium 6. The second part 10b of the second sleeve-shaped part 10 has or can have a relatively small cross section, which means that the bridge structure 3 in question can be made very narrow. This means that fastening members 11 in the bridge 3 can be made with a relatively small dimension or width B. The bridge can thus be made relatively narrow in the transverse direction on a jaw bone/soft tissue.

The first sleeve-shaped part 9 can be anchored in the implant by means of a screw 12. The screw head 12a extends level with the inclined transition surface 10c on the outside of the second sleeve-shaped part. The second sleeve-shaped part is guided against the first sleeve-shaped part via an inner surface 10a' on the first part 10a. In addition, the second sleeve-shaped part is guided against the outer surface 12a' of the screw head via an inner surface 10b' on the second part 10b. By means of this arrangement, the first and second sleeve-shaped parts 9 and 10 can on the one hand be joined together in the position shown in FIG. 1 and, on the other hand, can be separated so that the first sleeve-shaped part 9 can maintain its position according to the figure and the second sleeve-shaped part 10 can follow along with the bridge or can form an independent or free part when the bridge is to be detached temporarily from the implants, for example after testing. Definitive locking between the first and second parts can be obtained with, for example, the screw 12 which expands the first sleeve-shaped part 9 in the space 10d.

Figure 2:
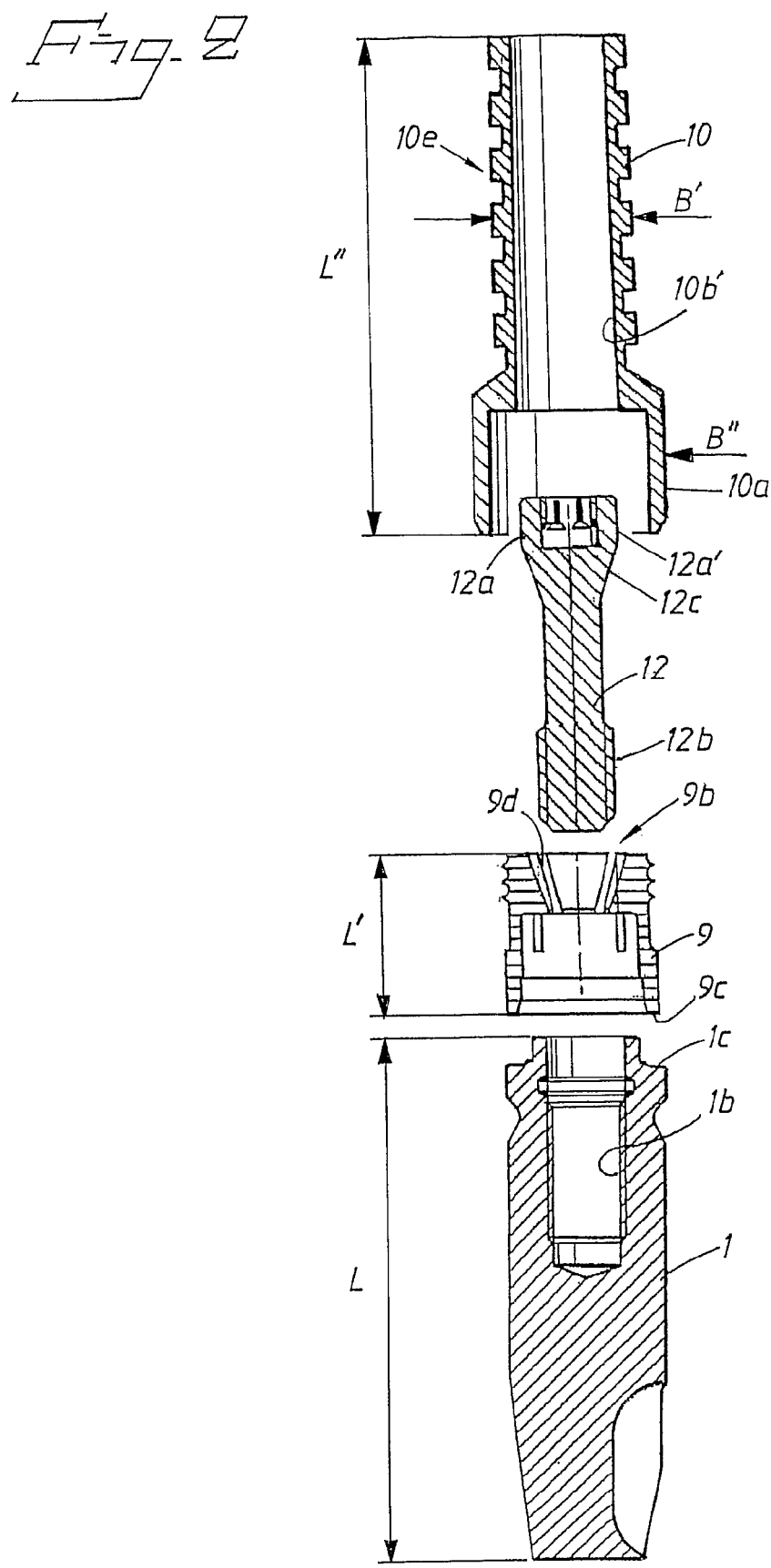
FIG. 2 shows a vertical and exploded view of implant and spacer member according to FIG. 1.

In FIG. 2, the various parts of implant 1, first sleeve part 9, screw 12, and second sleeve part 10 are shown separately and in detail. The implant 1 can be of a type known per se and can have a length L of likewise known type. The implant is provided inter alia with an internal thread 1b and an outer support flange 1c for the first sleeve-shaped part 9 which can bear against the flange 1c via an end surface 9c. At its upper parts, the first sleeve-shaped part is provided with spring arrangements by means of which the implant screw can be maintained in its position shown in FIG. 1. The implant screw comprises an outer thread 12b which can cooperate with the internal thread 1b in the implant. The screw has a cone-shaped outer surface 12c at its screw head 12a. This cone-shaped surface 12c can cooperate with a corresponding inclined cone-shaped surface 9d in the first sleeve-shaped part. The first sleeve-shaped part has a length or height L' which is about ⅓ of the length or height L of the implant. The second sleeve-shaped part 10 has a narrowed part with a width B' which can constitute ca. 70% of a width B" of the first part 10a of the second sleeve-shaped part. The second sleeve-shaped part has a length or height L" which can be approximately the same length as the length or height L of the implant. By means of the narrowed part, the bridge in question (see FIG. 3 in 30, FIG. 1) can be made relatively narrow in relation to the previously known technique according to the aforementioned WO document. The height or length L' of the first sleeve-shaped part corresponds substantially to the thickness of the soft tissue (see 5 in FIG. 1). By means of the arrangement shown, the first sleeve-shaped part can be considered as being extended downward in the region of the fibers 7 of the gingiva. By virtue of the fact that the first sleeve-shaped part remains in its position according to FIG. 1, any biological incorporation that has started does not have to be interrupted or destroyed if the bridge is to be removed after a time, e.g. for testing or adjustment. In FIG. 2, a portion of the second sleeve-shaped part cooperating with fastening member 11 is indicated symbolically by 10e. The length L' of the first sleeve-shaped part is approximately ⅓ of the length L" of the second sleeve-shaped part. The thickness of the soft tissue in FIG. 1 is indicated by T.

The invention is not limited to the embodiment described above by way of example, and instead it can be modified within the scope of the attached patent claims and the inventive concept.

The invention claimed is:

1. A method for orienting a bridge in position relative to a dental implant, the method comprising:
    coupling a first sleeve-shaped part of a spacer member to the dental implant using a screw;
    guiding an inner surface of a first portion of a second sleeve-shaped part against an outer surface of the first sleeve-shaped part;
    rotating the screw in a first direction to contact a cone-shaped surface of a head of the screw against an inner surface of the first sleeve-shaped part as the screw moves into the first sleeve part to_expand at least a portion of the first sleeve-shaped part such that the outer surface of the first sleeve-shaped part expands against the inner surface of the first portion of the second sleeve-shaped part to secure the second sleeve-shaped part to the first sleeve-shaped part;
    attaching a bridge to a second portion of the second sleeve-shaped part;
    rotating the screw in a second direction, opposite the first direction, to loosen the second sleeve-shaped part from the first sleeve-shaped part of the spacer member as the screw is withdrawn from the first sleeve part and at least a portion of the outer surface of the first sleeve-shaped part contracts; and
    removing the bridge along with the second sleeve-shaped part with the first sleeve-shaped part remaining attached to the implant.

2. The method as in claim 1, wherein assembling the first sleeve-shaped part further comprises expanding the first sleeve-shaped part to engage the inner surface of the first portion of the second sleeve-shaped part.

3. The method as in claim 2, wherein expanding the first sleeve-shaped part comprises expanding the first sleeve-shaped part by rotating the screw.

4. An arrangement for orienting a bridge in position relative to a dental implant, the arrangement comprising:
    a spacer member configured to cooperate with the dental implant to provide position orientation through cooperation with fastening members arranged in the bridge, wherein the spacer member comprises first and second sleeve-shaped parts, the first sleeve-shaped part being attachable to the dental implant using a screw, the first sleeve-shaped part comprising an expandable structure at an upper end thereof and outer and inner surfaces, the screw having a head with a cone-shaped surface configured to contact the inner surface of the first sleeve-shaped part such that rotation of the screw into the implant causes expansion of the expandable structure of the first sleeve-shaped part, the second sleeve-shaped part comprising an inner surface configured to mate against the outer surface of the first sleeve-shaped part such that the second sleeve-shaped part is secured to the first sleeve-shaped part;

wherein the outer surface of the first sleeve-shaped part is expanded against the inner surface of the second sleeve-shaped part upon expansion of the at least a portion of the first-sleeve shaped part for securing the second sleeve-shaped part to the first sleeve-shaped part; and wherein the second sleeve-shaped part comprises a portion that engages with a fastening member of the bridge for separating the second sleeve-shaped part from securement with the first sleeve-shaped part.

5. The arrangement as claimed in claim 4, wherein the first sleeve-shaped part has a length substantially corresponding to a thickness of a soft tissue or a gum on the jaw bone, in which the respective dental implant is applied.

6. The arrangement as claimed in claim 4, wherein the first sleeve-shaped part can be arranged in relation to and can cooperate with fibers of the gingiva.

7. The arrangement as in claim 4, wherein the first sleeve-shaped part cooperates with the dental implant via an upper flange surface on the dental implant.

8. The arrangement as in claim 4, wherein the second sleeve-shaped part has a lower sleeve-shaped portion which can be engaged on an upper portion of the first sleeve-shaped part, 9. The arrangement as claim 4, wherein the second sleeve-shaped part has a first part which can cooperate with the first sleeve-shaped part, and a second part which is narrower in relation to the first part and which supports the portion cooperating with a fastening member.

10. The arrangement as in claim 9, wherein the first and second upper parts merge on the outside via an inclined outer surface which adjoins the top surface of the soft tissue or gum.

11. The arrangement as in claim 10, wherein the narrowed part is included in a narrowed bridge construction.

12. The arrangement as in claim 11, wherein the first sleeve-shaped part for the respective implant can be anchored to the implant, and the first and second parts can be mutually guided in relation to one another by an internal screw with a head which extends, in the assembled state, substantially level with the inclined upper surface, 13. The arrangement as in claim 4, wherein the width of a second part of the second sleeve-shaped part is a diameter that is less than a diameter of the first sleeve-shaped part.

14. The arrangement as in claim 4, wherein the width of a second part of the second sleeve-shaped part is approximately 70% of the width of a first part of the second sleeve-shaped part.

15. The arrangement as in claim 4, wherein the second sleeve-shaped part comprises a plurality of protrusions along an outer surface thereof for engaging fastening members of a bridge.

16. The arrangement as in claim 4, wherein the first sleeve-shaped part comprises at least one longitudinal slot for facilitating expansion of the at least a portion of the first sleeve-shaped part.

17. The arrangement as in claim 16, wherein the first sleeve-shaped part comprises a plurality of longitudinal slots for facilitating expansion of the at least a portion of the first sleeve-shaped part, 18. The arrangement as in claim 4, wherein the first sleeve-shaped part comprises a lower sleeve-shaped portion that surrounds an upper portion of the implant.

19. The arrangement as in claim 18, wherein the lower sleeve-shaped portion of the first sleeve-shaped part abuts the upper portion of the implant.

20. The arrangement as in claim 4, wherein the inner surface of the first sleeve-shaped part is cone-shaped, 21. An arrangement for orienting a bridge in position relative to a dental implant, the arrangement comprising a spacer member configured to cooperate with the dental implant to provide position orientation through cooperation with fastening members arranged in the bridge, the spacer member comprising a first sleeve-shaped part and a second sleeve-shaped part, the first sleeve-shaped part having an expandable structure at an upper end thereof and outer and inner surfaces, the inner surface being cone-shaped and configured to be contacted by a surface of a head of a screw such that movement of the screw into the implant causes expansion of the expandable structure of the first sleeve-shaped part, the second sleeve-shaped part comprising an inner surface configured to mate against the outer surface of the first sleeve-shaped part when the first sleeve-shaped part is expanded such that the second sleeve-shaped part is secured to the first sleeve-shaped part, the second sleeve-shaped part further comprising a portion that engages with a fastening member of the bridge for separating the second sleeve-shaped part from securement with the first sleeve-shaped part.

22. The arrangement as in claim 21, wherein the first sleeve-shaped part comprises at least one longitudinal slot for facilitating expansion of the at least a portion of the first sleeve-shaped part.

23. The arrangement as in claim 22, wherein the first sleeve-shaped part comprises a plurality of longitudinal slots for facilitating expansion of the at least a portion of the first sleeve-shaped part.

24. The arrangement as in claim 21, wherein the inner surface of the first sleeve-shaped part is configured to be contacted against a cone-shaped surface of the head of the screw to cause expansion of the expandable structure of the first sleeve-shaped part.

* * * * *